United States Patent [19]
Fine et al.

[11] Patent Number: 5,866,134
[45] Date of Patent: Feb. 2, 1999

[54] METHOD FOR ENHANCING THE ANTIBODY RESPONSE TO SPECIFIC ANTIGENS WITH INTERLEUKIN-10

[75] Inventors: Jay S. Fine, Bloomfield; Michael J. Grace, Hamilton Township, both of N.J.

[73] Assignee: Schering Corporation, Kenilworth, N.J.

[21] Appl. No.: 410,199

[22] Filed: Mar. 24, 1995

[51] Int. Cl.[6] ................................................. A61K 39/385
[52] U.S. Cl. ................................... 424/195.11; 424/85.2; 424/234.1; 424/244.1; 424/278.1
[58] Field of Search ................................ 424/852, 278.1, 424/244.1, 234.1

[56] References Cited

U.S. PATENT DOCUMENTS 5,231,012  7/1993  Mosmann, et al. .................. 435/69.52
5,658,744  8/1997  Ochoa et al. ........................... 435/7.24

OTHER PUBLICATIONS

Faunterloy et al, Immunobiol 188:379–391, 1993.
Dick et al, Contrib. Microbiol. Immunol. 10:48–114, 1989.
Moore et al, Ann Rev. Immunol 11:165–190, 1993.
Gurg et al, J Immunol 152(4):1589–1596, (Feb. 15) 1994.
Richter, G et al, Cancer Res., vol. 53, Sep. 15, 1993, pp. 4134–4137.
Golding, B et al, Am. J. Trop. Med. Hgg., vol. 50(4) Suppl. 1994, pp. 33–40.
Nussler, A.K. et al, Parasitology, 1992, vol. 105, S5–523.
Allione, A et al, Cancer Res., 1994, vol. 54(23) pp. 6022–6026 (abs.).
Genzyme Research Products Catalog, pp. 92–93, Interleukin–10.

Primary Examiner—James C. Housel
Assistant Examiner—Ginny Allen Portner
Attorney, Agent, or Firm—Cynthia L. Foulke; Jaye McLaughlin

[57] ABSTRACT

A method for enhancing the immune response of a mammal to a vaccine comprising administering to such a mammal an effective amount of IL-10 in conjunction with the vaccine. A pharmaceutical composition comprised of an effective amount of IL-10, a natural, synthetic or recombinant antigen and a pharmaceutcally acceptable carrier.

19 Claims, 6 Drawing Sheets

METHOD FOR ENHANCING THE ANTIBODY RESPONSE TO SPECIFIC ANTIGENS WITH INTERLEUKIN-10

BACKGROUND OF THE INVENTION

Active immunization is the administration of an antigen to an animal to bring about an immune response in the animal. A vaccine against a microorganism is an antigenic preparation which when inoculated into a non-immune individual will confer active immunity to the microorganism but will not cause disease. Specificity and memory, the two key elements of the adaptive immune system, are exploited in vaccination, since the adaptive immune system mounts a much stronger response on second encounter with an antigen. This secondary immune response is both faster to appear and more effective than the primary response. The principle of vaccine development is to alter a microorganism or its toxins (natural antigens) in such a way that they become innocuous without losing antigenicity. Alternatively, antigenic polypeptides of the organism in question can be produced by recombinant methods or by synthetic chemistry to produce an effective vaccine.

One problem that frequently is encountered in the course of active immunization is that the antigens used in the vaccine are not sufficiently immunogenic to raise antibody titer to sufficient levels to provide protection against subsequent challenge, or to maintain the potential for mounting these levels over extended time periods. Another problem is that the vaccine may be deficient in inducing cell-mediated immunity which is a primary immune defense against bacterial and viral infection. Still another problem is that an individual patient might be immunocompromised due to illness or age.

To obtain a stronger humoral and/or cellular response, it is common to administer a vaccine in a formulation containing an adjuvant. An adjuvant is a substance that enhances, nonspecifically, the immune response to an antigen, or which causes an individual to respond to an antigen who would otherwise without the adjuvant not respond to the antigen. An adjuvant is usually administered with an antigen, but may also be given before or after antigen administration.

However, in spite of the many advances in vaccines and vaccine preparation, very often vaccines do not give the immunogenic response desired especially in the immuno-compromised and the aged. An example is the pneumococcal vaccine PNU-IMUNE 23. Pneumococcal pneumonia is currently the most common cause of bacterial pneumonia in the United States, and the rate of this disease is especially high in the elderly, young children, patients with predisposing conditions such as asplenia, chronic heart, lung and kidney disease, diabetics and patients suffering from genetic or acquired immunosuppression (Breiman et. al. *Arch. Intern. Med.* 150: 1401–1404 (1990)). These groups are at greater risk of pneumococcal spread to the blood and the central nervous system which is the most common cause of bacterial meningitis. This vaccine has a aggregate efficacy of approximately 75% in immunocompetent adults, but the coverage in the high-risk groups listed above has been debated, and is certainly much lower (Butler et. al. *J. Am. Med. Assoc.* 270: 1826 (1993). Thus, there is a need for additional aids or adjuvants which can be administered in conjunction with a vaccine to bring about an immunizing effect to the aged and immunocompromised.

SUMMARY OF THE INVENTION

It has been surprisingly discovered that Interleukin-10 fills this need as an effective vaccine adjuvant.

Accordingly, the present invention provides a method for enhancing the immune response of a mammal to a vaccine comprising administering to a mammal in need of vaccination an effective amount of IL-10 in conjunction with a vaccine.

Preferably, the mammals treated will be humans and the IL-10 utilized will be one of the human allotypes. In a preferred embodiment the humans will be immunocompromised.

The present invention further provides for a pharmaceutical composition comprising an effective amount of IL-10, a natural, synthetic or recombinant antigen, and a pharmaceutically acceptable carrier.

The IL-10 dosage for the mammals will be administered preferably by subcutaneous injection or intravenous infusion and will be in the amount of 2 to 150 micrograms ($\mu$g) per kilogram (kg) of body weight per day. Most preferably, the IL-10 dosage will be in an amount of 2 to 80 micrograms per kilogram body weight per day. Alternatively, the mammals will be pre-treated with IL-10 for 1–4 days prior to vaccination, and then be continued on IL-10 therapy. Preferably, the IL-10 will be administered simultaneously with the vaccine, from 1 to 14 days prior to or after the administration of the vaccine in an amount of about 2 to 150 micrograms ($\mu$g) per kilogram of body weight, preferably, 2 $\mu$g–80 $\mu$g per kilogram of body weight.

DETAILED DESCRIPTION OF THE INVENTION

Figure 1A:
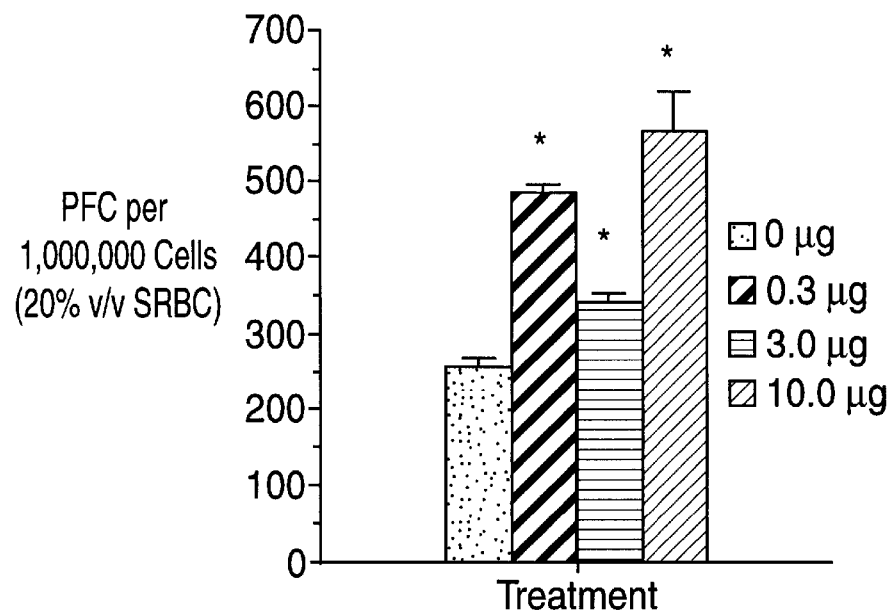
FIGS. 1(*a*) and 1(*b*) are graphic representations of the increase in the specific primary splenic plaque-forming cell antibody response to sheep erythrocytes observed in vivo in mice dosed with IL-10.

IL-10 was originally described as a T helper 2 (Th2) cell product which inhibited the production of cytokines such as interferon-$\gamma$ by Th1 cells (Fiorentino et. al. *J. Exp. Med.* 170: 2081–2095 (1989)) and enhanced the proliferation of mouse thymocytes in response to IL-2 and IL-4 (Suda, et. al. *Cell. Immunol.* 129: 228–240 (1990)). Subsequently, IL-10 was found to inhibit, in the presence of monocyte/macrophages, both the proliferation and cytokine synthesis of human T cells and T cell clones (deWaal Malefyt et. al. *J. Exp. Med.* 174: 915–924 (1991); Taga and Tosato, *J. Immunol.* 148: 1143–1148 (1992)) and mouse T cell clones (Ding and Shevach, *J. Immunol.* 148 :3133–3139 (1992)).

IL-10 is normally produced by mouse Th2 clones, B cell lymphomas, T cells, activated mast cell lines, activated macrophages, keratinocytes and CD5+ B cells (Fiorentino et. al. *J. Exp. Med.* 170: 2081–2095 (1989); Moore et. al. *Science* 248: 1230–1234 (1990); O'Garra et. al. *Int. Immunol.* 2: 821–832 (1990); MacNeil et. al. *J. Immunol.* 145: 4167–4173 (1990); Fiorentino et. al. *J. Immunol.* 147: 3815–3821 (1991); Hisatsune et. al. *Lympokine Cytokine Res.* 11: 87–93 (1992); Lin et. al., *Ann. NY Acad. Sci.* 651: 581–583 (1992).

In addition to the effects of IL-10 listed above, IL-10 has been reported to possess an array of B lymphocyte stimulatory properties in in vitro experimental models. B cells play an important role in the host immune response by producing antibodies in response to foreign antigen. IL-10 was found to up-regulate the surface expression of class II major histocompatability complex antigens on murine small dense B cells (Fei Go et. al. *J. Exp. Med.* 172: 1625–1631 (1990)), augment the proliferation of activated human tonsillar B cells and induce their differentiation into antibody secreting cells (Rousset et. al. *Proc. Natl. Acad. Sci.* USA 89: 1890–1893 (1992)) capable of secreting immunoglobulin M (IgM), IgG1, IgG3, and, in concert with TGFβ, IgA (Defrance et. al. *J. Exp. Med.* 175: 671–682 (1992); Briere et. al. *J, Exp. Med.* 179: 757–762 (1994)). IL-10 was also found to differentially regulate immunoglobulin production in the presence of different cytokines (Pencanha et. al. *J. Immunol.* 148: 3427–3432 (1992)). In vivo administration of anti-IL-10 antibody to mice from birth until 8 weeks reduced serum IgM and IgA and in vivo antibody responses to two bacterial antigens, increased serum IgG2a and IgG2b levels and impaired the generation and function of CD5+ B cells in the peritoneum (Ishida et. al. *J. Exp. Med.* 175: 1213–1220 (1992)). These in vivo effects of anti-IL10 administration were attributed to an increase in endogenous interferon-γ levels.

Despite this body of evidence indicating that IL-10 is capable of inducing polyclonal immunoglobulin levels in vitro, to date there have been no reports on the ability of IL-10 to enhance the antigen-specific antibody response in vivo or in vitro. The production of specific antibodies directed against specific foreign antigens is one of the initial responses of the immune system and is an important factor in determining how rapidly infectious agents are cleared from the host. We have found that in vivo and in vitro IL-10 administration enhances the antigen-specific antibody response to two distinct antigens in mice, namely sheep erythrocytes and the pneumococcal vaccine PNU-IMUNE 23. The ability of IL-10 to enhance the humoral response to PNU-IMUNE 23 is of special interest because Pneumococcal pneumonia is currently the most common cause of bacterial pneumonia in the United States, and the rate of this disease is especially high in the elderly, young children, patients with predisposing conditions such as asplenia, chronic heart, lung and kidney disease, diabetics and patients suffering from genetic or acquired immunosuppression (Breiman et. al. *Arch. Intern. Med.* 150: 1401–1404 (1990)). These groups are at greater risk of pneumococcal spread to the blood and the central nervous system which is the most common cause of bacterial meningitis. This vaccine has a aggregate efficacy of approximately 75% in immunocompetent adults, but the coverage in the high-risk groups listed above has been debated, and is certainly much lower (Butler et. al. *J. Am. Med. Assoc.* 270: 1826 (1993).

The results of the Examples show below show that IL-10 restores the antibody response to the pneumococcal vaccine in aged mice to levels observed in young mice. Thus, IL-10 can be used in augmenting the humoral immune response in immunosuppressed patients, the elderly and patients suffering from hypogammaglobulinemia.

Accordingly, the present invention provides a method for enhancing the immune response of a mammal to a vaccine comprising administering to a mammal in need of vaccination an effective amount of IL10 in conjunctive with a vaccine. The term "in conjunction with" as used herein refers to the administration of IL-10 concurrently, before or following administration of vaccine.

As used herein, "interleukin-10" or "IL-10" can be either human IL-10 (h IL-10) or murine IL-10. Human IL-10 is defined as a protein which (a) has an amino acid sequence substantially identical to a known sequence of mature (i.e., lacking a secretory leader sequence) hIL-10 as disclosed in U.S. patent application Ser. No. 07/917,806, filed Jul. 20, 1992, which corresponds to International Application No. PCT/US90/03554, Publication No. WO 91/00349, and (b) has biological activity that is common to native hIL-10.

IL-10 can be obtained from culture media of activated T-cells capable of secreting the protein. Preferentially, however, it is obtained by recombinant techniques using isolated nucleic acids encoding for the IL-10 polypeptide. General methods of molecular biology are described, e.g., by Sambrook, et al., *Molecular Cloning, A Laboratory Manual*, Cold Spring Harbor Publish., Cold Spring Harbor, N.Y., 2d ed. 1989 and by Ausubel et al., (eds.) *Current Protocols in Molecular Biology*, Green/Wiley, New York (1987 and periodic supplements). The appropriate sequences can be obtained from either genomic or cDNA libraries. Polymerase chain reaction (PCR) techniques can be used. See, e.g., *PCR Protocols: A Guide to Methods and Applications*, 1990, Innis et al., (Ed.), Academic Press, New York, N.Y.

Libraries are constructed from nucleic acid extracted from appropriate cells. See, for example, International Application Publication No. WO 91/00349, which discloses recombinant methods to make IL-10. Useful gene sequences can be found, e.g., in various sequence data bases, e.g., Gen Bank and EMBL for nucleic add, and PIR and Swiss-Prot for protein, c/o Intelligenetics, Mountain View, Calif., or the Genetics Computer Group, University of Wisconsin Biotechnology Center, Madison, Wis.

Clones comprising sequences that encode human IL-10 (hIL-10) have been deposited with the American Type Culture Collection (ATCC), Rockville, Md., under Accession Numbers 68191 and 68192. Identification of other clones harboring the sequences encoding IL-10 is performed by either nucleic acid hybridization or immunological detection of the encoded protein, if an expression vector is used. Oligonucleotide probes based on the deposited sequences are disclosed in International Application Publication No. WO 91/00349. Oligonucleotide probes useful for identification of the sequences can also be prepared from conserved regions of related genes in other species. Alternatively, degenerate probes based on the amino acid sequence of IL-10 can be used.

Various expression vectors can be used to express DNA encoding IL-10. Conventional vectors used for expression of recombinant proteins used for expression of recombinant proteins in prokaryotic or eukaryotic cells may be used. Preferred vectors include the pcD vectors described by Okayama et al., *Mol. Cell. Bio.* Vol. 3: 280–289 (1983); and Takebe et al., *Mol. Cell. Biol.* Vol. 8: 466–472 (1988). Other SV40-based mammalian expression vectors include those disclosed in Kaufman et al., *Mol. Cell. Biol.* Vol. 2: 1304–1319 (1982) and U.S. Pat. No. 4,675,285. These SV40-based vectors are particularly useful in COS7 monkey cells (ATCC No. CRL 1651), as well as in other mammalian cells such as mouse L cells and CHO cells.

Standard transfection methods can be used to produce eukaryotic cell lines which express large quantities of the polypeptide. The process of the present invention is a process to purify IL-10 expressed by eukaryotic cells from a cell supernatant into which the protein was expressed. Eukaryotic cell lines include mammalian, yeast and insect cell lines. Exemplary mammalian cell lines include COS-7 cells, mouse L cells and Chinese Hamster Ovary (CHO) cells. See Sambrook et al., supra and Ausubel et al., supra. Methods for purifying biologically active IL-10 are described in International Patent Application Serial No. PCT/US94/01909 filed Mar. 3, 1994.

Adjuvant activity is manifested by a significant increase in immune-mediated protection by development of an immune response in an individual who otherwise would not respond at all to a vaccine. Enhancement of humoral immunity is typically manifested by a significant increase in the titer of antibody raised to the antigen.

According to the present invention, mammals are administered an effective amount of IL-10 simultaneously or prior to treatment with the indicated vaccine antigen to increase the amount of antibody specific for the particular antigen. The amount of vaccine administered will be according to the manufacturer's instructions. The effective amount of IL-10 is defined as any amount that will increase the amount of a antibody against a specific antigen. The term "effective amount" as used herein regarding the effective amount of IL-10 administered in accordance with the present invention means an amount of IL-10 which produces an increase in antibody level sufficient to provide increased protection from an infectious agent than if a vaccine had been administered without IL-10. Preferably, the increase will be an increase of at least 25%. Preferably, the mammals will be treated with IL-10 derived from a human source, ie. human IL-10 produced by recombinant techniques from *E. coli* or CHO cells. The dosage for the mammals will be administered by subcutaneous injection or intravenous infusion and will be in the amount of 2 to 150 $\mu$g per kilogram of body weight per day. Preferably, the dosage will be in an amount of 2 to 80 $\mu$g per kilogram body weight per day, and most preferably 2–25 $\mu$g.

The amount, frequency and period of administration will vary, depending on a variety of factors, including the level of serum antibody, the age of the patient, nutrition, etc. The administration will initially be daily and may continue throughout the patient's lifetime. Dosage amount and frequency may be determined during the initial screenings and the amount of IL-10 on the magnitude of the response.

To complement the antigen-specific antibody response, it may be useful to administer the IL-10 in conjunction with other biologically and/or pharmaceutically active compounds. For example, it can be combined with other agents shown to enhance B cell responses, such as interleukin-4, interleukin-7, interleukin-13 or interleukin-14. Additionally, the vaccine antigen may be administered in the presence of other adjuvants to boost the response even further.

The methods of the present invention to provide administration of IL-10 in conjunction with a vaccine has the following advantages. The total antigenic load of vaccine to be administered may be reduced since less antigen in the presence of IL-10 would elicit an immunologic response at least equivalent to that achieved by the administration of the normal amount of the vaccine. Since less antigen would be required per vaccination by administering IL-10 in accordance with the present invention, the probability of undersirable side-effects associated with some vaccines currently in use would be reduced.

The immune response of certain types of individuals who respond poorly to vaccination would be enhanced by administering IL-10 in conjunction with a vaccine. Types of individuals who should benefit from the methods of the present invention include (1) those types having impaired immune responsiveness, due to illness or age for example those humans 55 years or older; (2) those individuals who appear normal but who are nevertheless nonresponsive to certain vaccines as well as; (3) individuals undergoing immunosuppressive therapies such as radiation and chemotherapy.

Thus, we have discovered an effective method for (1) enhancing an effective primary immune response in mammals to antigens present in a vaccine; (2) enhancing an effective level of antibodies in mammals exposed to antigens in vaccines wherein the immune response by the mammal without the administration of IL-10 would not be strong enough or fast enough to prevent disease.

Vaccines contemplated for use in accordance with the present invention include but are not limited to bacterial vaccines, toxoid vaccines (inactivated toxins) and viral vaccines or mixtures thereof used for active immunization. See for example chapter 75 entitled "Immunizing Agents" in Reminton's Pharmaceutical Sciences 14th Edition 1990 Mack Publishing Co. p 1426–1441 and the antitoxins, toxoids, vaccines and live vaccines approved by the U.S. Food and Drug Administration and listed on page 208–209 (Product Category Index) of the Physician's Desk Reference, 46th Ed. 1992. Suitable bacterial vaccines include bacterial vaccines against the following disease entities or states: cholera, pertussis, plague, typhoid fever, meningitis, pneumococcal pneumonia, *H. influenzae* type B, leprosy, gonorrhea, Group B meningococcus, and Group B streptococcus, Gram-negative sepsis, *E. coli* sepsis, and *Pseudomonas aeruginosa*. Suitable toxoids include diphtheria toxoid, botulism toxid, and tetanus toxoid. The suitable "multiple antigens" include diphtheria and tetanus toxoids, the triple antigen-diphtheria, pertussis and tetanus toxoids such as are available from Connaught Laboratories, Inc. Swiftevater, Pa. 18370.

In addition, the IL-10 will typically be used to enhance the protection afforded by vaccines that are considered "weak" (i.e., provide diminished protection in terms of level, extent, and/or duration). Examples of such vaccines are bacterins such as Bordetella bacterin, *Escherichia coli* bacterins, Haemophilus bacterins, Leptospirosis vaccines, *Moraxella bovis* bacterin, Pasteurella bacterin and *Vibrio fetus* bacterin, and pneumococcal vaccines.

The IL-10 will normally be administered separately from the vaccine, although it may be administered in combination with the vaccine. When IL-10 is combined with the vaccine, the composition administered contains an immunogen that is effective in eliciting a specific response to a given pathogen or antigen, a pharmaceutically acceptable vaccine carrier and an immunopotentiating amount of IL-10. Administration of IL-10 can be subcutaneous, intravenous, parenteral, intramuscular, or any other acceptable method. Preferably, IL-10 is administered prior to the administration of the vaccine and at the same site where the vaccine is to be administered. The formulations and pharmaceutical compositions contemplated by the above dosage forms can be prepared with conventional pharmaceutically acceptable excipients and additives, using conventional techniques. Other adjuvants may be administered either with the vaccine or together with the IL-10.

If multiple doses of the vaccine are to be administered over a period of time, additional IL-10 may be administered in conjunction with each subsequent dose of the vaccine. The amount of IL-10 which is administered with each subsequent dose of the vaccine may be more, the same or less than the amount of IL-10 administered in conjunction with the initial dose of the vaccine. The amount of IL-10 administered with each subsequent dose of the vaccine will depend upon the antibody response of the patient after the first dose of the vaccine.

Solutions of IL-10 to be administered may be reconstituted from lyophilized powders and they may additionally contain preservatives buffers, dispersants, etc. Preferably, IL-10 is reconstituted with any isotonic medium normally utilized for subcutaneous injection, e.g., preservative-free sterile water.

The effect of IL-10 on enhancing the immune response of a vaccine is illustrated by the following non-limiting data which should not be construed to limit the scope of the disclosure.

Example 1

To determine the effect of in vivo IL-10 treatment on the primary antibody response to sheep red blood cells (SRBC), IL-10 was administered to young DBA/2 mice by intraperitoneal injection at 0.3, 3 or 10 μg per day for 5 days. Control mice received vehicle only (10 mM Tris, pH 7.4). Two to four hours after the first injection of IL-10 or vehicle, the mice received an intravenous injection (0.2 mls) of a 20%, 2% or 0.2% vol/vol dilution of SRBC.

After 5 days, spleen cells from each mouse were prepared by harvesting the intact spleen, mashing the spleen in Dulbecco's phosphate buffered saline with the blunt end of a 5 ml syringe plunger followed by trituration, and passage through 75 μM nylon mesh. The spleen cells were counted and their viability determined by trypan blue dye exclusion.

To measure the spleen plaque-forming cell antibody response, the procedure originally described by Jerne and Nordin (*Science* 140: 405–407 (1963)) was used with minor modifications. Briefly, 200,000 spleen cells in 50 microliters were added to tubes previously incubated at 42° C. containing 200 microliters of a 1% w/v SeaPlaque Agarose solution and 50 microliters of a 50% v/v SRBC solution. The tubes were hand-vortexed and the contents poured onto the center of a glass slide and spread over two-thirds of the slide. After air-drying for 5–10 minutes, the slides were inverted, placed on a plaque tray filled with RPMI 1640 medium and incubated for 1 hour at 37° C., 5% $CO_2$ in a humidified chamber. The slides were then blotted dry of excess liquid and placed in a new plaque tray containing guinea pig complement diluted 1:50 in cold RPMI 1640. After a 4 hour incubation at 37° C., 5% $CO_2$ in a humidified chamber, the slides were carefully removed, the excess liquid blotted and incubated overnight at 4° C. in another plaque tray containing RPMI 1640. Plaques were enumerated the following day using a magnifying glass and a Manostat Colony Counter and the number of plaques normalized per one million spleen cells.

Figure 1B:
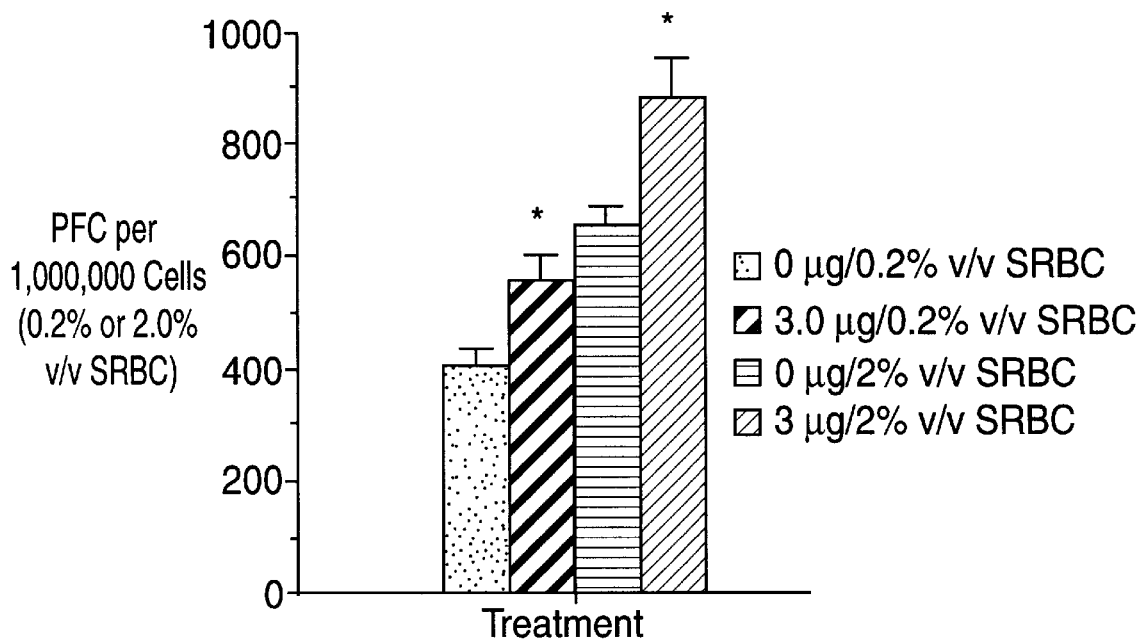

The results, as shown in FIGS. 1(a) and 1(b) demonstrate that in vivo treatment of DBA/2 mice with 0.3–10 μg IL-10 per day produced a statistically significant increase in the number of PFC per million spleen cells following immunization with 20% sheep red cells (top) or 0.2 and 2% SRBC (bottom).

Example 2

To demonstate the effect of IL-10 on the secondary IgG response to the SRBC antigen, DBA/2 mice were injected intravenously with SRBC twice four weeks apart and IL-10 treatment begun at the time of the second immunization as described above.

Figure 2:
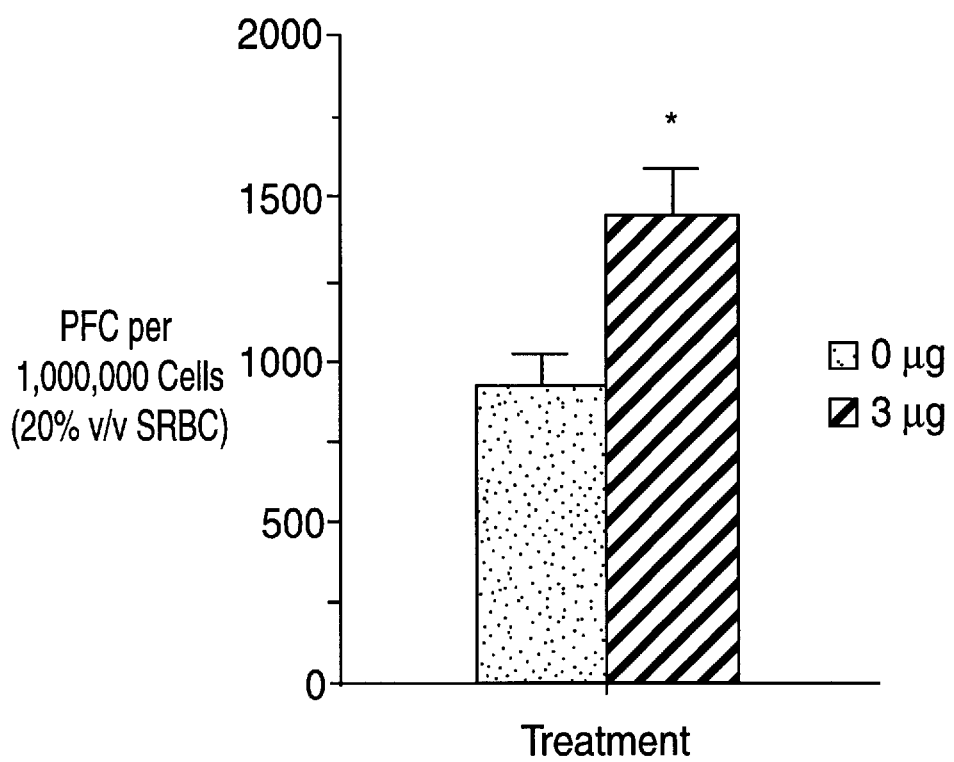
FIG. 2 is a graphic representation of the enhancement of the specific secondary splenic plaque-forming cell antibody response to sheep erythrocytes observed in vivo in mice dosed with IL-10.

The indirect PFC response was determined 5 days after the second injection by a further modification of the Jerne slide method described above (Nordin et. al. *J. Immunol.* 103: 859–863 (1969). An additional set of slides were prepared for each animal which was incubated in RPMI 1640 for one hour as in the direct assay. The slides were then placed in a new plaque tray and incubated with 0.5 mg/ml Concanavalin A to block IgM activity. After a two hour incubation, these slides were rinsed in DPBS and placed on new plaque trays containing 100 μg/ml rabbit anti-mouse IgG for one hour. The slides were then transferred to new plaque trays containing guinea pig complement for 3 hours. The slides were then blotted and stored at 4° C. until the next day when there were counted. As shown in FIG. 2, treatment with 3 μg IL-10 at the time of secondary immunization resulted in a statistically significant increase in the number of PFC per one million spleen cells compared to mice treated with vehicle.

Together, the results illustrated in FIGS. 1(a) and 1(b) indicate that in vivo IL-10 treatment significantly enhances both the primary and secondary antibody response to the SRBC antigen.

Example 3

To determine whether IL-10 treatment can also enhance the antibody response to the polysaccharide vaccine PNU-IMUNE 23, young (4 to 5 month old) and old (22 month old) BALB/c mice were immunized with 11.5 μg PNU-IMUNE vaccine by intraperitoneal injection and treated daily with IL-10 or vehicle by intraperitoneal injection.

Five days after immunization with PNU-IMUNE 23, the mice were sacrificed and the spleen cells isolated as above. The PFC response to the PNU-IMUNE antigen was assayed as described previously (Garg and Subbarao, *Infect. Immunity* 60: 164–169 (1992)). SRBC were washed three times in saline and coupled with the PNU-IMUNE vaccine in the presence of chromium chloride (CrCl3). The coupled SRBC were then washed three times to remove any free vaccine and CrCl3. The direct PFC assay was performed as described above. In some experiments, SRBC were coupled to bovine serum albumin using the same concentration of CrCl3 to ensure that the PFC response being measured was vaccine-specific, as has been shown previously Garg and Subbarao, *Infect. Immunity* 60: 164–169 (1992); Garg, Kaplan and Bondada *J. Immunol.* 152: 1589–1595 (1993)).

Figure 3A:
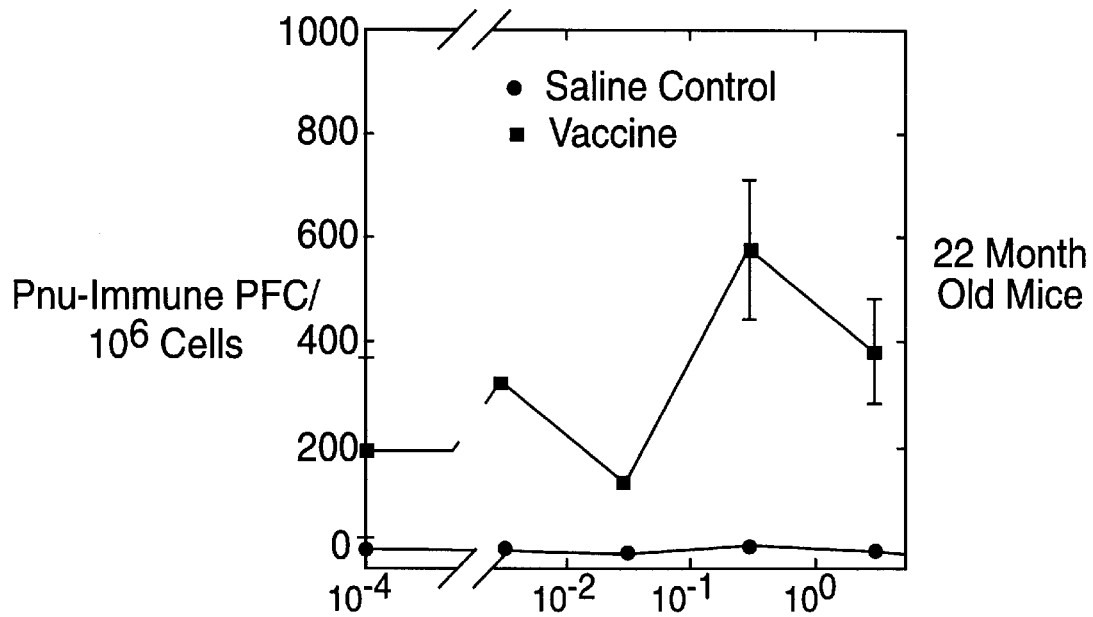
FIGS. 3(*a*) and 3(*b*) are graphical representations of the increase in the splenic plaque-forming cell response to the Pnu-imune 23 response in aged (22 month) mice (top) versus young (4–5 months) (bottom) following in vivo IL-10 administration.
Figure 3B:
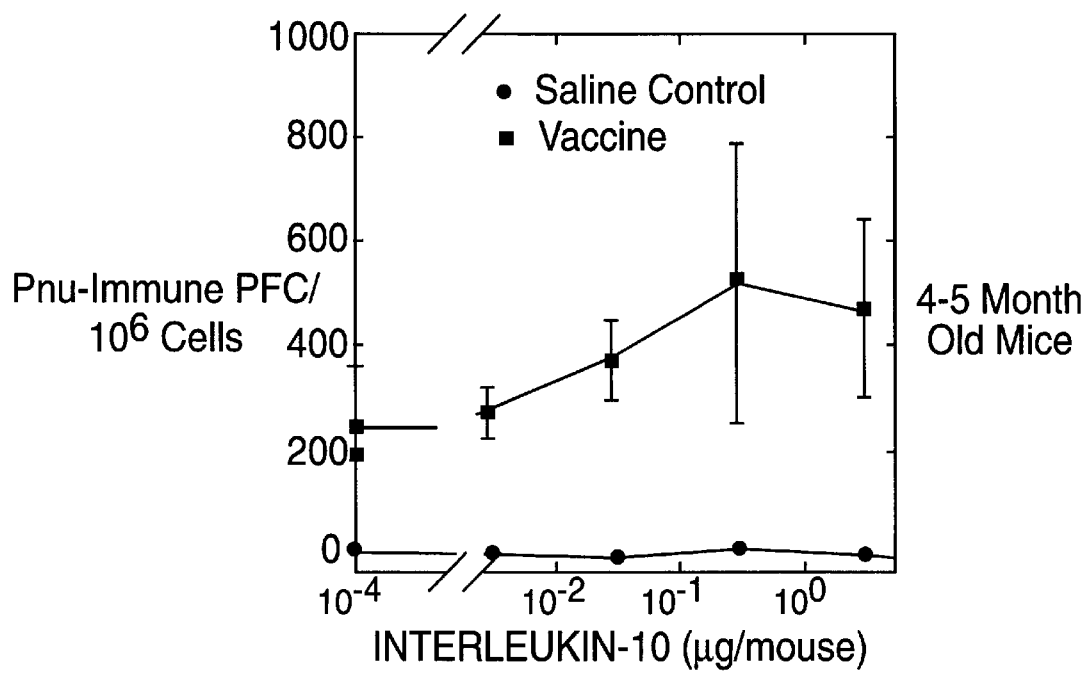

As shown in FIGS. 3(a) and 3(b) IL-10 significantly enhanced the PFC response to the vaccine in old mice, whereas there was no effect on the response in young mice. A dose of 0.3 μg IL-10 was optimal in increasing the vaccine response in the old mice.

Example 4

The in vivo effect of IL-10 was reproduced in an in vitro culture system to define the cellular requirements of the vaccine repsonse (Garg, Kaplan and Bondada *J. Immunol.* 152: 1589–1595 (1993)). For these studies, spleen cells from unimmunized mice (young and old) were isolated as specified above and then cultured in a 1:1 mixture of Iscove's modified Dulbecco's modified Eagle's medium and Ham's F-12 medium supplemented with 10% fetal calf serum, transferrin, insulin and trace elements as previously described (Mosier *J. Immunol.* 127: 1490–1494 (1981)).

Varying doses of PNU-IMUNE 23 vaccine and IL-10 were added at the time of initiation of the cultures and the cells incubated at 37° C., 5% $CO_2$ in a humidified atmosphere for five days. The numbers of vaccine specific PFC were quantitated as described above. Previous work has shown that the vaccine coupled SRBC are effective in detecting the PFC response to 21 of 23 polysaccharides comprising the vaccine (Garg, Kaplan and Bondada *J. Immunol.* 152: 1589–1595 (1993)). The ability of spleen cells from old mice to make a PFC response to this vaccine is especially compromised under these in vitro culture conditions.

Figure 4A:
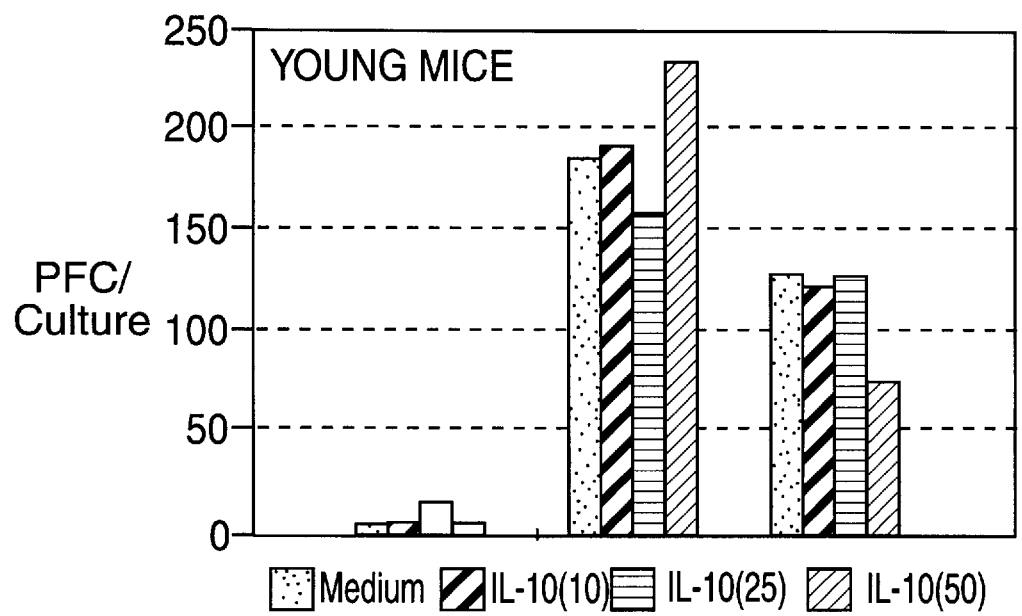
FIGS. 4(*a*) and 4(*b*) are graphic representations of the in vitro plaque-forming cell concentration-response observed when spleen cells from young (top) or aged (bottom) mice were incubated with various concentrations of IL-10 and the PNU-IMUNE vaccine.
Figure 4B:
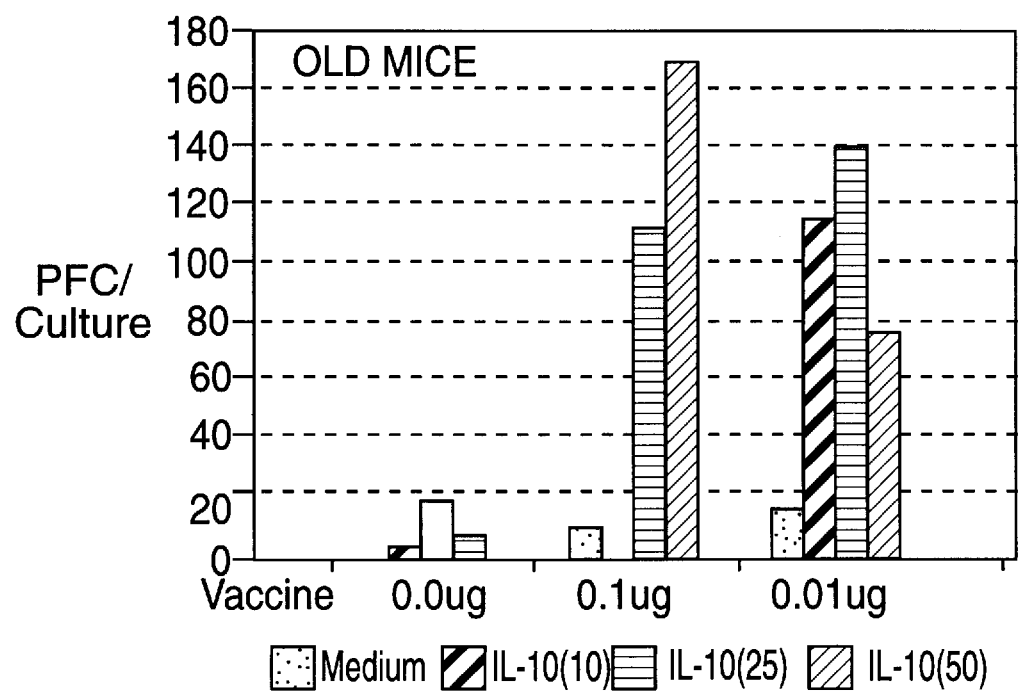

As shown in FIGS. 4(*a*) and 4(*b*) both 25 and 50 U/ml IL-10 (which are equivalent to 6 and 12 μg/ml respectively) were able to restore the PFC response to cultures of spleen cells from old mice treated with 0.1 μg PNU-IMUNE 23, and all concentrations of 10–50 U/ml IL-10 were able to restore the response of spleen cells from old mice to 0.01 μg PNU-IMUNE. In contrast, the baseline PFC response of spleen cells from young mice was much higher that that of old mice and all concentrations of IL-10 tested had no effect on this response.

Figure 5:
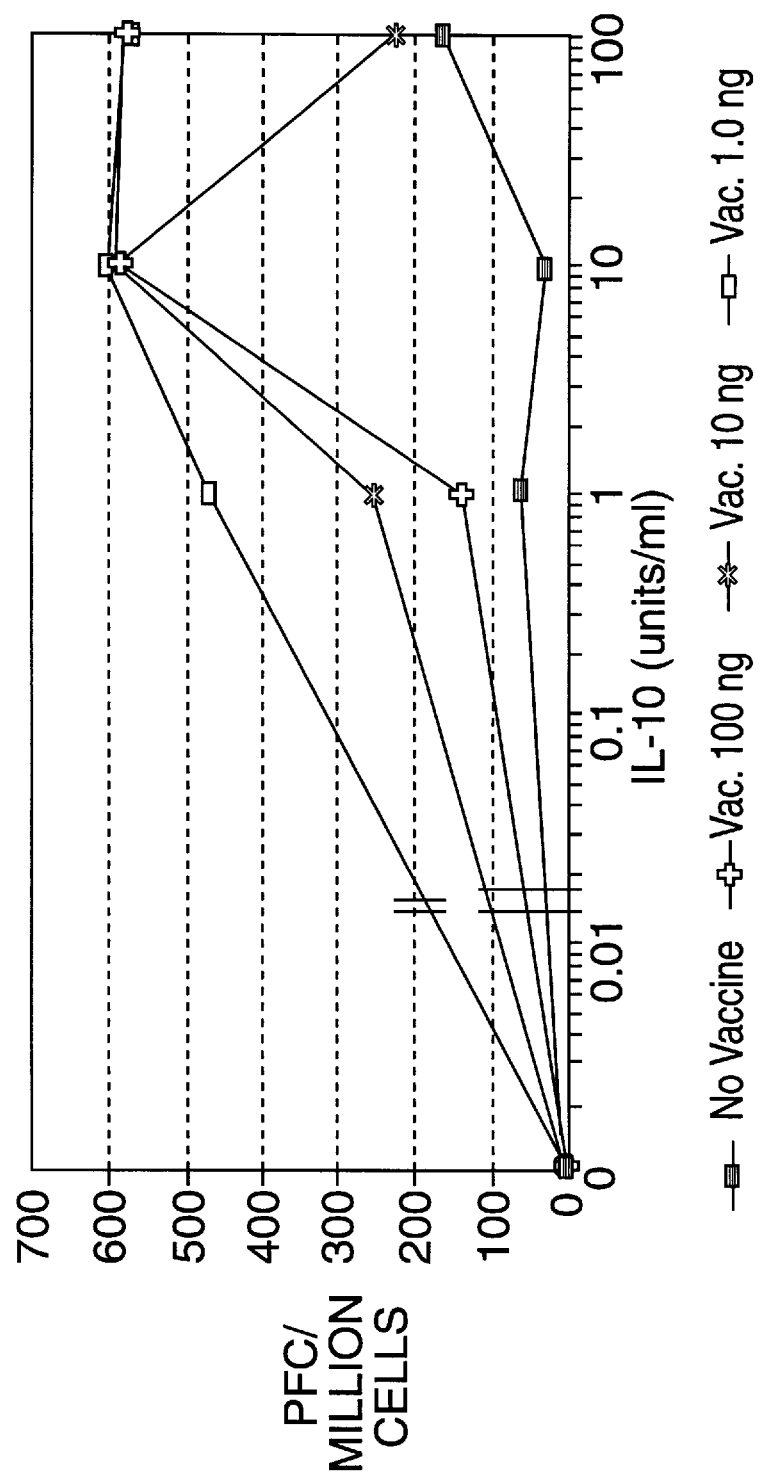
FIG. 5 illustrates the in vitro PFC results when spleen cells from old mice were incubated in vitro with varying concentrations of IL-10 and PNU-IMUNE vaccine.

Further studies, as illustrated in FIG. 5, show that 1–100 U/ml IL-10 (which are equivalent to 0.25 and 25 μg/ml respectively) was able to significantly enhance the PFC response of spleen cells from old mice to 1–100 ng of vaccine in culture. These results indicate that IL-10 is capable of significantly augmenting the antibody response to PNU-IMUNE 23 vaccine in cultures of spleen cells from old mice. This augmentation appears to result in the restoration of the response to levels observed normally in young mice.

Example 5

In order to further understand the effect of IL-10 in enhancing/restoring the antibody response to the vaccine, the ability of IL-10 to increase the PFC response in the absence of T lymphocytes was evaluated. Spleen cells from old mice were treated with antibodies to specific T cell surface markers (Thy 1.2, CD4 and CD8) and rabbit complement to eliminate T cells from the responding population. The Concanavalin A induced proliferative response of the resulting population was reduced by 95% following T cell depletion, indicating that T cells were nearly completely eliminated.

Figure 6B:
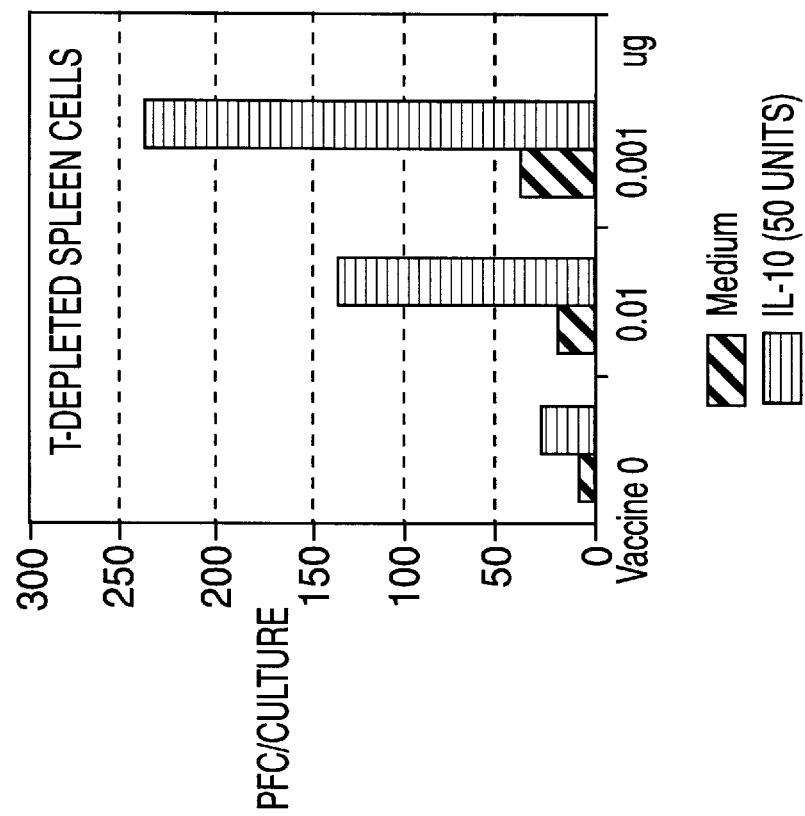
FIGS. 6(*a*) and 6(*b*) are graphic representations of the in vitro effect of IL-10 on the PFC response when unfractionated or T cell-depleted splenocytes from aged mice were incubated with IL-10 in the presence of the PNU-IMUNE vaccine.
Figure 6A:
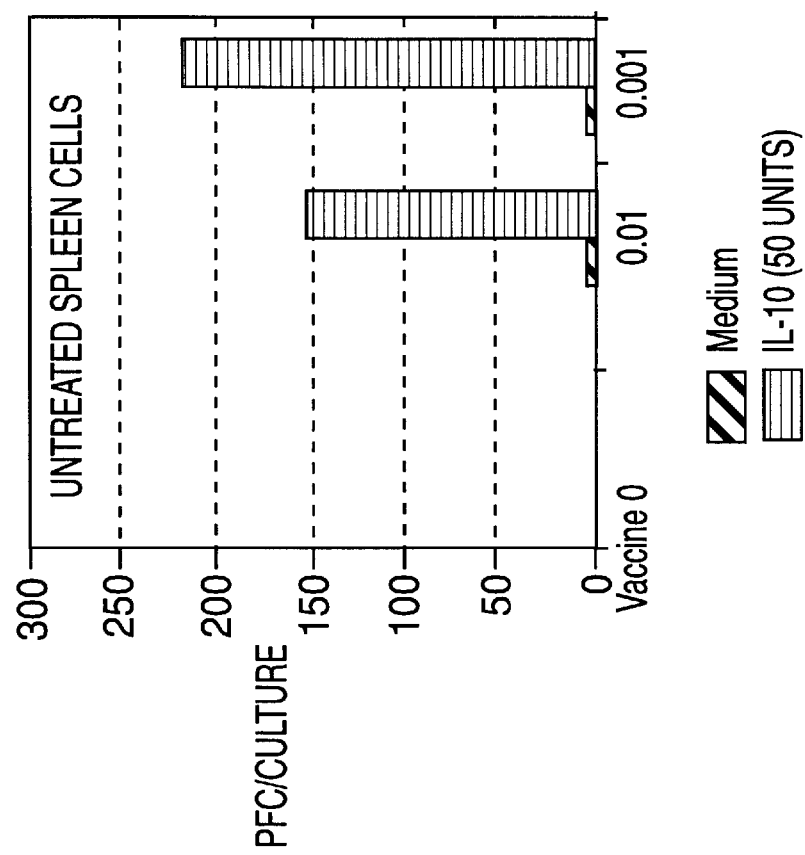

As shown in FIGS. 6(*a*) and 6(*b*) these T-depleted spleen cells responded to the PNU-IMUNE vaccine when supplemented with IL-10 in a manner similar to intact spleen preparations. These data suggest that the adjuvant effect of IL-10 in old mice does not require the obligate presence of T lymphocytes. IL-10 may be acting directly on B cells to promote their proliferation and/or differentiation response to the vaccine. Alternatively, IL-10 may be affecting macrophages or dendritic cells in the responding population and thus indirectly enhance the B cell response.

While the present invention has been described in conjunction with the specific embodiments set forth above, many alternatives, modifications and variations thereof will be apparent to those of ordinary skill in the art. All such alternatives, modifications and variations are intended to fall within the spirit and scope of the present invention, which is only to be limited by the claims.

What is claimed is:

1. A method for enhancing an immune response of a mammal to a polysaccharide vaccine comprising administering to a mammal in need of vaccination an effective amount of Interleukin-10 (IL-10) in conjunction with the vaccine.

2. The method of claim 1 wherein the mammal is human.

3. The method of claim 1 wherein the mammal is immunocompromised.

4. The method of claim 3 wherein the mammal is immunocompromised due to age.

5. The method of claim 1 wherein the IL-10 is administered in an amount of 2–150 μg per kilogram of body weight.

6. The method of claim 5 wherein the IL-10 is administered in an amount of 2–80 μg per kilogram of body weight.

7. The method of claim 5 wherein the IL-10 is administered in an amount of 25 μg per kilogram of body weight.

8. The method of claim 1 wherein the IL-10 is administered 2–4 days prior to the administration of the vaccine.

9. The method of claim 1 wherein the vaccine is a pneumococcal polysaccharide vaccine.

10. A method for enhancing an immune response of a mammal to a polysaccharide vaccine wherein the mammal is immunocompromised due to age comprising:

administering to said mammal an immune-response enhancing amount of Interleukin-10 (IL-10) in conjunction with a polysaccharide vaccine.

11. The method of claim 10 wherein the IL-10 is administered in an amount of 2–150 μg per kilogram of body weight.

12. The method of claim 11 wherein the amount of IL-10 which is administered is 2–80 μg per kilogram of body weight.

13. The method of claim 10 wherein the mammal is a human.

14. The method of claim 10 wherein the IL-10 is administered 2–4 days prior to the administration of the vaccine.

15. A pharmaceutical composition comprising an immunological enhancing amount of Interleukin-10 (IL-10); and a vaccine.

16. The pharmaceutical composition of claim 15 wherein the IL-10 is contained within a sustained release formulation.

17. A kit for enhancing an immunogenic response of a mammal to antigens in a polysaccharide vaccine comprising a container of a pharmaceutical composition of Interleukin-10 (IL-10), and a pharmaceutically acceptable carrier therefor; and a container of a polysaccharide vaccine.

18. The kit claim 17 wherein the IL-10 is contained within a sustained release formulation.

19. The kit of claim 18 wherein the vaccine is a pneumococcal polysaccharide vaccine.

* * * * *